United States Patent [19]
Tarbit et al.

[11] Patent Number: 5,744,615
[45] Date of Patent: Apr. 28, 1998

[54] ULTRA WHITE N,N'-ETHYLENE-BIS (TETRABROMOPHTHALIMIDE) AND ITS PRODUCTION IN AQUEOUS ACETIC ACID

[75] Inventors: Brian Tarbit, Ashington; Brian Adger, Hexham; Paul Willett, Witton-le-Wear, all of England

[73] Assignee: Great Lakes Chemical, Frauenfeld, Switzerland

[21] Appl. No.: 588,624

[22] Filed: Jan. 19, 1996

Related U.S. Application Data

[62] Division of Ser. No. 259,344, Jun. 14, 1995, Pat. No. 5,508,429.
[51] Int. Cl.$^6$ .................................................. C07D 403/04
[52] U.S. Cl. ............................. 548/462; 548/461; 524/94

[58] Field of Search ........................... 548/462, 461; 524/94

[56] References Cited

U.S. PATENT DOCUMENTS 5,317,048    5/1994    Tarbit et al. ............................ 524/94

*Primary Examiner*—E. Rollins Buffalow
*Attorney, Agent, or Firm*—Woodard, Emhardt, Naughton, Moriarty & McNett

[57] ABSTRACT

Disclosed is a process for producing an ultra-white N,N'-ethylene-bis(tetrabromophthalimide) product useful as a flame retardant. Also disclosed is a flame retardant composition predominantly comprised of N,N'-ethylene-bis(tetrabromophthalimide) and having unprecedented color and high purity.

7 Claims, No Drawings

ULTRA WHITE N,N'-ETHYLENE-BIS (TETRABROMOPHTHALIMIDE) AND ITS PRODUCTION IN AQUEOUS ACETIC ACID

This application is a division of application No. 08/259, 344, filed Jun. 14, 1995 now U.S. Pat. No. 5,508,429.

BACKGROUND

The present invention relates generally to fire retardants for use in polymer compositions and the like. More particularly, the present invention relates to an ultra-white N,N'-ethylene-bis-(tetrabromophthalimide) composition and to a method for its production.

Fire retardant compositions are performance chemicals that must meet exacting standards to gain acceptance and widespread use in industry. Among requirements for flame retardants, color is of particular importance. For a majority of applications, it is desired that the flame retardant be as white as possible. This enables production of high quality white plastics, but is also important because polymer processors require that colors of end products result from the particular pigment utilized rather than its combination with the color of the flame retardant.

Another important characteristic of flame retardants is purity, for example as can be shown by thermogravimetric analysis. Flame retardant materials that have significant impurities which decompose, volatilize or sublime at polymer processing temperatures can cause undesired color, blowing and other problems in batches into which they are incorporated. Therefore, improved flame retardant materials will also demonstrate stability to higher temperatures in thermogravimetric analysis.

One material receiving substantial attention as a flame retardant is N,N'-ethylene-bis-(Tetrabromophthalimide) (EBT). However, acceptance of EBT compositions in industry has severely lagged largely because EBT compositions thus far available have been too yellow.

SUMMARY OF THE INVENTION

Accordingly, it is an object of this invention to provide a uniquely white EBT composition for use as a flame retardant.

Another object of the invention is to provide a method for producing a uniquely white EBT composition.

Another object of the invention is to provide a polymer composition and articles produced therefrom comprising the uniquely white EBT composition.

Still another object of the invention is to provide a white EBT composition of high purity as can be demonstrated for example by thermogravimetric analysis.

These and other objects of the invention are achieved by preferred embodiments of the present invention, one of which provides a process for preparing a highly white N,N'-ethylene-bis(tetrabromophthalimide) product. This process comprises reacting ethylene diamine and tetrabromophthalic anhydride in aqueous acetic acid to produce N,N'-ethylene-bis(tetrabromophthalimide). The N,N'-ethylene-bis(tetrabromophthalimide) is then recovered in a white precipitate, which is dried, so as to form a N,N'-ethylene-bis(tetrabromophthalimide) product having a yellowness index of about 5 or less. Advantageously, the product also has less than 1% weight loss in thermogravimetric analysis to 400° C. In a particularly preferred mode, this process is achieved by the steps of slurrying tetrabromophthalic anhydride into aqueous acetic acid, adding ethylene diamine to the slurry at a temperature of at least about 80° C. to form a reaction mixture, reacting the reaction mixture at a temperature of at least about 120° C. to achieve at least 70% conversion to N,N'-ethylene-bis (tetrabromophthalimide), recovering a precipitate from the reaction mixture including the N,N'-ethylene-bis (tetrabromophthalimide), and drying the precipitate to obtain a white particulate product predominantly comprised of N,N'-ethylene-bis(tetrabromophthalimide).

Another preferred embodiment of the invention relates to a flame retardant composition predominantly comprised of N,N'-ethylene-bis-(tetrabromophthalimide) and having a yellowness index of about 5 or less. Advantageously, the product also has less than 1% weight loss in thermogravimetric analysis to 400° C. EBT compositions of this embodiment also preferably have a whiteness index of about 65 or greater. Such EBT compositions have unprecedented color quality in combination with other advantageous features further described below.

Additional objects, features and advantages of the present invention will be apparent from the following description.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated, a feature of this invention is the production of a highly white N,N'-ethylene-bis(tetrabromophthalimide) product by reacting ethylene diamine and tetrabromophthalic anhydride in an aqueous acetic acid medium. It has been discovered that by conducting this reaction in an aqueous acetic acid medium, EBT products of unprecedented whiteness and high purity can be obtained.

In this regard, it will be understood that the acetic acid used as the reaction medium is preferably of high purity. For example, the use of acetic acid of 99%+ purity is preferred, and such grades are commercially available from many sources.

The aqueous acetic acid medium may be a 1% to 99% aqueous solution of acetic acid, although the medium will usually be at least 3% acetic acid. Importantly, it has been found that the high quality white product of the invention can be produced in this wide range of aqueous acetic acid reaction mediums, also having the desirable high purity as exhibited by TGA. As additional features of the invention, advantages attach to processes conducted in dilute acetic acid and to those conducted in more concentrated acetic acid. For example, processes conducted in dilute acetic acid, say about 3% to about 10% acetic acid solutions, minimize reaction medium and reaction medium disposal costs. On the other hand, processes conducted in more concentrated aqueous acetic acid, say at least about 80% aqueous acetic acid, generate lower reaction pressures and offer other advantages such as those related to recovery of acetic acid in the medium.

In another aspect of the invention, the aqueous acetic acid mother liquors from a previous reaction medium can be reused in subsequent processes to generate the high quality white EBT product. The mother liquors can optionally be treated by distillation or the like prior to reuse.

Tetrabromophthalic anhydride ("TBPA") suitable for use in the process of the invention is commercially available. Particle sizes ranging up to 1000 microns or more are suitable for use in the invention, although it is preferable to use micronized material with an average particle diameter of less than about 50 microns. Additionally, the acid number of the TBPA is desirably less that about 0.2 mg/g to prevent formation of impurities, for example those which may be related to salts of the ethylene diamine.

As known and as used herein, ethylene diamine ("EDA") refers to 1,2-diaminoethane. This material is also available from commercial sources, and for use in the present invention preferably assays at 99%+ purity. In particular, it is highly desirable that the ethylene diamine be free from water and carbonate.

As to specific synthesis details, it is preferred to first provide a slurry of tetrabromophthalic anhydride in the aqueous acetic acid medium. This slurry may be formed in the reaction vessel, or may be formed and then provided to the reaction vessel. As will be understood, the reaction vessel utilized will be able to withstand the pressure generated by the use of the acetic acid medium at the specified reaction temperatures.

The slurry is preheated to a temperature between about 80° and about 160° C., preferably about 90° to about 120° C., with agitation. This preheating can be for several hours or more but is preferably for a period up to about 1 hour. Thereafter, the EDA is added while the slurry remains at a temperature of about 80° to about 160° C., more preferably about 90° to about 120° C. The addition of EDA can be carried out over 1–2 hours or more, but is preferably carried out in less than about 10 minutes and more preferably less than about 5 minutes, for instance about 2 minutes or less. The addition of EDA, which may be in neat form or in a suitable solvent (in small amounts to maintain the essentially aqueous acetic acid reaction medium sufficient to achieve the superior product color), is desirably achieved by blowing the EDA into the reaction vessel under pressure of an inert gas such as nitrogen to ensure a rapid addition and to ensure against hang-up in the lines. In this regard, it is of course important that the addition of EDA be carried out in such a manner that the momentary increase in pressure in the reaction vessel does not exceed the head pressure of the EDA addition system or the pressure limit of the particular operating system employed.

As will be understood, the EDA will be added in essentially stoichiometric amount (i.e. essentially a 1:2 molar ratio) with respect to the TBPA. That is, about 1 mole of EDA will be added for every 2 moles of TBPA in the slurry. It is important that this stoichiometric ratio be maintained since variations from it can lead to discolored product. For this reason, it is most preferable that the molar ratio of EDA to TBPA be kept in the range of 1:1.9 to 1:2.1. In highly advantageous reactions thus far, EDA to TBPA molar ratios of 1.01 to 2.00 have been employed while still acheiving 100% conversion of the TBPA to the amidic acid intermediate.

After EDA addition, the reaction is conducted at a temperature of about 110° to about 250° C., more preferably about 120° to about 180° C., with those temperatures above about 150° C. being most preferred. The water of reaction can remain in the reaction mixture, which can be agitated using conventional and commercially available agitation systems. Surprisingly, it has been discovered that significant conversion to the final cyclized EBT product can be achieved in the aqueous acetic acid reaction medium, in some instances ranging above about 25% and even up to about 50% or more. Conversion to the cyclized EBT product can be determined, for instance, by observing the water event (which occurs upon cyclization of the amidic acid intermediate to form the EBT final product) by thermogravimetric analysis ("TGA"). In applicants' work, desirable reactions conducted at temperatures of about 160° to about 170° C. have been continued for periods in the range of 10 hours or more to achieve significant conversion to the cyclized EBT product, although this duration will of course vary in accordance with factors su(such as the temperature of reacting. The pressure of reacting has thus far been the autogenous pressure of the reaction mixture at the reaction temperature used, or slightly higher due to the pressurized nitrogen gas used during addition of the EDA. The pressure generated will of course vary with the particular temperature chosen and reaction medium chosen, with higher temperatures and more aqueous reaction mediums generating higher pressures, and vice versa.

After the reaction, the reaction mixture can be cooled to about 20° to about 100° C., more typically 80° to about 100° C., and the solids (typically up to about 40 weight % of the reacted medium and more preferably about 5% to about 30% of the reacted medium) can be isolated, e.g. by conventional centrifugation. The isolated product may then be washed, but it has advantageously been discovered that such washing is unnecessary to produce the high quality white products herein described. The isolated solid EBT composition is dried, preferably at elevated temperature, to remove acetic acid and to complete residual cyclization to the EBT product. The drying and residual cyclization can be conducted at any temperature, but this step is preferably conducted at a temperature of at least about 175° C. and more typically at least about 200° C. The duration of the drying will vary in accordance with many factors such as the particular drying temperature used and the qualities of the EBT material being dried. The drying will in any event be of sufficient temperature and duration to essentially complete the residual cyclization to form a predominantly EBT product, which can be monitored by TGA. After this drying and completion of cyclization, a uniquely white EBT product is obtained, readily having a yellowness index of about 5 or less. In this regard, EBT products having yellowness indexes of about 4 or less are readily obtained. The EBT products typically have acid numbers of about 1 mg/g or less and more typically 0.5 mg/g or less. Bromine contents of the EBT products are usually at least about 65% and more usually about 65% to about 69%. Additionally, the resultant white EBT product will typically have superior purity as has been demonstrated by TGA. For example, typical products have 1% weight loss at a temperature above about 400° C. in TGA. Typical products also have melting point onsets above about 445° C., for instance usually in the range of about 460° C. and above.

The EBT product can be milled during and/or after the drying operations, for example as occurs in a Winkworth plough share type mixer. The dried product is then preferably micronized to provide an average particle diameter of about 5 microns or less, more preferably about 2 microns or less.

Another embodiment of the invention provides a flame retardant composition predominantly (i.e. about 95% or more) comprised of N,N'-ethylene-bis-(tetrabromophthalimide) and having a yellowness index of 5 or less. Desirably, the product also has less than 1% weight loss in thermogravimetric analysis to 400° C. This composition may be produced for example by the process described above and more particularly detailed in the Examples below. In this regard, as will be understood, the "yellowness index" is determined in accordance with ASTM 1313 as can be measured by colorometer. EBT compositions of this embodiment also preferably have a "whiteness index" (ASTM 1313) of about 65 or greater, more preferably about 70 or greater, and are advantageously at least 98% comprised of the EBT product. Other preferred aspects of compositions of this embodiment are as set forth in the discussion of the first embodiment above and in the Examples which follow. The EBT compositions of the invention are of unprecedented color and TGA quality and represent a highly significant improvement over materials previously reported in the literature or commercially available.

The EBT product of the invention can be incorporated as a flame retardant in virtually any flammable material, natural or man-made, but will usually be incorporated in flammable synthetic polymers using conventional compounding techniques. For instance, the EBT product may be incorporated into crosslinked or non-crosslinked polymers of olefinic monomers, for example ethylene, propylene and butylene homopolymers or their copolymers with other polymerizable monomers; polymers of styrenic monomers, e.g. high-impact polystyrene and styrene copolymers; polyurethanes; polyamides; polyimides; polycarbonates; polyethers; acrylic resins; polyesters, e.g. poly(ethyleneterephthalate) and poly(butyleneterephthalate; epoxy resins; alkyl resins; phenolics; elastomers, for example butadiene/styrene copolymers and butadiene/acrylonitrile copolymers; terpolymers of acrylonitrile, butadiene and styrene; natural rubber; butyl rubber; polysiloxanes; wool; cellulose; polyvinylchlorides, etc.

As will be understood, the level of EBT product incorporated into the flammable material will vary widely in accordance with many factors such as the particular flammable material used, the application contemplated, other additives present, etc. Typically, the EBT will be incorporated at levels between about 1% and 50% of the total system weight, and more commonly between about 5% and 30% of the total system weight.

It will be understood that other conventional additives may also be incorporated into the flammable material. For example, the EBT product can be incorporated along with other flame retardant materials such as oxides of Group V elements, especially antimony oxides. Additional conventional additives may include antioxidants, antistatic agents, colorants, fibrous reinforcements, fillers, foaming/blowing agents, catalysts, heat stabilizers, impact modifiers, lubricants, plasticizers, processing aids, UV light stabilizers, crosslinking/curing agents, etc.

In order to promote a further appreciation and understanding of the present invention and its features and advantages, the following examples are provided. It will be understood that these examples are illustrative, and not limiting, of the invention. Percentages given herein are percentages by weight unless indicated otherwise. Color analyses in the Examples were performed with a Minolta Tricolorstimulus colorometer in accordance with ASTM 1313.

EXAMPLE 1

To a 1 liter stainless steel autoclave fitted with overhead stirrer, vent, pressure gauge, temperature probe, pressurized addition funnel and with a heated oil jacket was added TBPA (150 g., 0.323 mole, 2 micron) water (600 mls) and acetic acid (20 mls). The resulting slurry was heated to 96° C. and ethylene diamine (9.7 g., 0.162 mole) added using nitrogen pressure over 10 seconds. The reaction was then heated to 170° C. These conditions where held for 16 hours. The reaction was then cooled to 50° C. and filtered. The product was then dried at 200° C. on a fluid bed drier. A white product was obtained showing the following characteristics.

| | |
|---|---|
| 1% weight loss | 363° C. |
| 10% weight loss | 482° C. |
| Impurity level | n/d |
| Whiteness index | 72.1 |
| Yellowness index | 4.28 |
| Acid number | 0.5 |

EXAMPLE 2

To a 10 l. stainless steel autoclave fitted with overhead stirrer, vent, pressure gauge, temperature probe, pressurized addition funnel and with a heated oil jacket was added TBPA (1500 g., 3.23 mole, 2 micron) water (6000 mls) and acetic acid (200 mls). The resulting slurry was heated to 96° C. and ethylene diamine (97 g., 1.62 mole) added using nitrogen pressure over 10 seconds. The reaction was then heated to 170° C. These conditions where held for 16 hours. The reaction was then cooled to 50° C. and filtered. The product was then dried at 200° C. on a fluid bed drier. A white product was obtained showing the following characteristics.

| | |
|---|---|
| 1% weight loss | 419° C. |
| 10% weight loss | 488° C. |
| Impurity Level | (n/d) |
| Whiteness index | 75.89 |
| Yellowness index | 3.59 |
| Acid number | 0.35 |

EXAMPLE 3

To a 10 l. stainless steel autocalve fitted with overhead stirrer, vent, pressure gauge, temperature probe, pressurized addition funnel and with a heated oil jacket was added TBPA (1500 g., 3.23 mole, 2 micron) water (6000 mls) and acetic acid (200 mls). The resulting slurry was heated to 96° C. and ethylene diamine (97 g., 1.62 mole) added using nitrogen pressure over 10 seconds. The reaction was then heated to 170° C. These conditions where held for 16 hours. The reaction was then cooled to 50° C. and filtered. The product was then dried at 200° C. on a fluid bed drier. A white product was obtained showing the following characteristics.

| | |
|---|---|
| 1% weight loss | 414° C. |
| 10% weight loss | 476° C. |
| Impurity Level | n/d |
| Whiteness index | 78.2 |
| Yellowness index | 3.24 |
| Acid number | 0.29 |

EXAMPLE 4

To a 10 l. stainless steel autoclave fitted with overhead stirrer, vent, pressure gauge, temperature probe, pressurized addition funnel and with a heated oil jacket was added TBPA (1500 g., 3.23 mole, 2 micron) water (6000 mls) and acetic acid (200 mls). The resulting slurry was heated to 96° C. and ethylene diamine (97 g., 1.62 mole) added using nitrogen pressure over 10 seconds. The reaction was then heated to 170° C. These conditions where held for 16 hours. The reaction was then cooled to 50° C. and filtered. The product was then dried at 200° C. on a fluid bed drier. A white product was obtained showing the following characteristics.

| | |
|---|---|
| 1% weight loss | 416° C. |
| 10% weight loss | 484° C. |
| Whiteness index | 76.86 |
| Yellowness index | 3.01 |
| Acid number | 0.16 |

EXAMPLE 5

To a 1 l. stainless steel autoclave fitted with overhead stirrer, vent, pressure gauge, temperature probe, pressurized addition tunnel and with a heated oil jacket was added TBPA (150 g, 0.323 mole, 2 micron) water (600 mls) and acetic acid (60 mls). The resulting slurry was heated to 170° C. These conditions were held for 16 hours. The reaction was then cooled to 50° C. and filtered. The product was then oven dried at 200° C. A white product was obtained showing the following characteristics (n/d= not detectable). This and other runs demonstrate that products with yellowness indexes in the range of about 2 to about 5 are readily obtained without further purification or treatment.

| | |
|---|---|
| Impurity Level | n/d |
| Whiteness index | 75.3 |
| Yellowness index | 2.4 |

EXAMPLE 6

To a 1 l. stainless steel autoclave fitted with overhead stirrer, vent, pressure gauge, temperature probe, pressurized addition funnel and with a heated oil jacket was added TBPA (150 g, 0.323 mole, 2 micron) water (520 mls) and acetic acid (130 mls). The resulting slurry was heated to 96° C. and ethylene diamine (9.7 g, 0.162 mole) added using nitrogen pressure over 10 seconds. The reaction was then heated to 170° C. These conditions were held for 16 hours. The reaction was then cooled to 50° C. and filtered. The product was then oven dried at 200° C. A white product was obtained showing the following characteristics.

| | |
|---|---|
| Impurity Level | n/d |
| Whiteness index | 73.1 |
| Yellowness index | 3.6 |

EXAMPLE 7

To a 1 l. stainless steel autoclave fitted with overhead stirrer, vent, pressure gauge, temperature probe, pressurized addition funnel and with a heated oil jacket was added TBPA (150 g, 0.323 mole, 2 micron) water (300 mls) and acetic acid (300 mls). The resulting slurry was heated to 96° C. and ethylene diamine (9.7 g, 0.162 mole) added using nitrogen pressure over 10 seconds. The reaction was then heated to 170° C. These conditions were held for 16 hours. The reaction was then cooled to 50° C. and filtered. The product was then oven dried at 200° C. A white product was obtained showing the following characteristics.

| | |
|---|---|
| Impurity Level | n/d |
| Whiteness index | 69.8 |
| Yellowness index | 3.7 |

EXAMPLE 8

To a 1 l. stainless steel autoclave fitted with overhead stirrer, vent, pressure gauge, temperature probe, pressurized addition funnel and with a heated oil jacket was added TBPA (150 g, 0.323 mole, 2 micron) water (130 mls) and acetic acid (520 mls). The resulting slurry was heated to 96° C. and ethylene diamine (9.7 g, 0.162 mole) added using nitrogen pressure over 10 seconds. The reaction was then heated to 170° C. These conditions were held for 16 hours. The reaction was then cooled to 50° C. and filtered. The product was then oven dried at 200° C. A white product was obtained showing the following characteristics.

| | |
|---|---|
| Impurity Level | n/d |
| Whiteness index | 65.8 |
| Yellowness index | 4.6 |

EXAMPLE 9

To a 1 l. glass autoclave fitted with overhead stirrer, vent, pressure gauge, temperature probe, pressurized addition funnel and with a heated oil jacket was added TBPA (150 g, 0.323 mole, 2 micron) water (20 mls) and acetic acid (600 mls). The resulting slurry was heated to 96° C. and ethylene diamine (9.7 g, 0.162 mole) added using nitrogen pressure over 10 seconds. The reaction was then heated to 170° C. These conditions were held for 16 hours. The reaction was then cooled to 50° C. and filtered. The product was then oven dried at 200° C. A white product was obtained showing the following characteristics.

| | |
|---|---|
| Impurity Level | n/d |
| Whiteness index | 68.6 |
| Yellowness index | 4.0 |

What is claimed is:

1. A polymer material comprising a flame retardant composition about 95° or more by weight comprised of N,N'-ethylene-bis(tetrabromophthalimide), said flame retardant composition having a yellowness index of about 5 or less and about 1% or less weight loss in thermogravimetric analysis to 400° C.

2. A molded or extruded article formed from a polymer material according to claim 1.

3. The polymer material of claim 1 which includes a polymer selected from the group consisting of crosslinked and non-crosslinked polymers of olefinic monomers.

4. The polymer material of claim 3 which includes a polymer selected from the group consisting of homopolymers or copolymers of propylene and butylene; polymers of styrenic monomers; polyurethane; polyamides; polyimides; polycarbonates; polyethers; acrylic resins; polyesters; alkyl resins; phenolic resins; butadiene-styrene copolymers; butadiene-acrylonitrile copolymers; terpolymers of acrylonitrile, butadiene and styrene; natural rubber; butyl rubber; polysiloxanes; wool; cellulose; and, polyvinylchlorides.

5. The polymer material of claim 4 which includes high-impact polystyrene.

6. The polymer material of claim 3, wherein the overall polymer material is comprised about 1% to about 50% by weight of said flame retardant composition.

7. The polymer material of claim 6, wherein the overall polymer material is comprised about 5% to about 30% by weight of said flame retardant composition.

* * * * *

UNITED STATES PATENT AND TRADEMARK OFFICE
CERTIFICATE OF CORRECTION

PATENT NO.   : 5,744,615
DATED        : April 28, 1998
INVENTOR(S)  : Brian Tarbit et al.

It is certified that error appears in the above-identified patent and that said Letters Patent is hereby corrected as shown below:

On Section 62 of the cover page, please delete "Jun. 14, 1995" and insert in lieu thereof --Jun. 14, 1994--.

In col. 1, line 5, please delete "Jun. 14, 1995" and insert in lieu thereof --Jun. 14, 1994--.

In col. 1, line 35, please delete "Tetrabromophthalimide" and insert in lieu thereof --tetrabromophthalimide--.

In col. 4, line 11, please delete "su(such" and insert in lieu thereof --such--.

In col. 7, line 12, please delete "tunnel" and insert in lieu thereof --funnel--.

Signed and Sealed this

Sixteenth Day of March, 1999

Attest:

Q. TODD DICKINSON

*Attesting Officer*   *Acting Commissioner of Patents and Trademarks*